US012569423B2

(12) United States Patent
Maleville

(10) Patent No.: US 12,569,423 B2
(45) Date of Patent: Mar. 10, 2026

(54) AMYLOSE/CAROTENOIDS COMPLEXATION PROCESS

(71) Applicant: ECLYPSE INK BIOTECHNOLOGY, Muret (FR)

(72) Inventor: David Maleville, Muret (FR)

(73) Assignee: ECLYPSE INK BIOTECHNOLOGY, Muret (FR)

( * ) Notice: Subject to any disclaimer, the term of this patent is extended or adjusted under 35 U.S.C. 154(b) by 504 days.

(21) Appl. No.: 17/916,506

(22) PCT Filed: Apr. 1, 2021

(86) PCT No.: PCT/EP2021/058592
§ 371 (c)(1),
(2) Date: Sep. 30, 2022

(87) PCT Pub. No.: WO2021/198410
PCT Pub. Date: Oct. 7, 2021

(65) Prior Publication Data
US 2023/0149280 A1 May 18, 2023

(30) Foreign Application Priority Data
Apr. 1, 2020 (FR) ...................................... 2003267

(51) Int. Cl.
*A61K 8/60* (2006.01)
*A61K 8/31* (2006.01)
*A61Q 1/02* (2006.01)

(52) U.S. Cl.
CPC ................. *A61K 8/60* (2013.01); *A61K 8/31* (2013.01); *A61Q 1/025* (2013.01); *A61K 2800/43* (2013.01)

(58) Field of Classification Search
None
See application file for complete search history.

(56) References Cited

U.S. PATENT DOCUMENTS 5,593,503 A * 1/1997 Shi .......................... A21D 2/186
127/65

OTHER PUBLICATIONS

Kong et al. Encapsulation and stabilization of β-carotene by amylose inclusion complexes, Food Research International, vol. 105, 2018, pp. 446-452, https://doi.org/10.1016/j.foodres.2017.11.058. (Year: 2018).*

Kim et al. Preparation of aqueous dispersion of b-carotene nano-composites through complex formation with starch dextrin, Food Hydrocolloids, 2013, 33, 256-263, http://dx.doi.org/10.1016/j.foodhyd.2013.04.001 (Year: 2013).*

Yang et al. Effect of microwave irradiation on internal molecular structure and physical properties of waxy maize starch, Food hydrcolloids, 2017, 69, 473-482, http://dx.doi.org/10.1016/j.foodhyd.2017.03.011 (Year: 2017).*

Corralo Spada et al. Microencapsulation of b-carotene using native pinhao starch modified pinhao starch and gelatin by freeze-drying, International Journal of Food Science and Technology 2012, 47, 186-194, doi:10.1111/j.1365-2621.2011.02825.x (Year: 2012).*

International Search Report for PCT/EP2021/058592, mailed Jul. 16, 2021, 3 pages.

Written Opinion of the ISA for PCT/EP2021/058592, mailed Jul. 16, 2021, 5 pages.

Kong et al., "Encapsulation and stabilization of [beta]-carotene by amylose inclusion complexes", Food Research International, Amsterdam, NL, vol. 105, 1, ISSN: 0963-9969, XP055753008, Mar. 2018, pp. 446-452.

Heinemann C et al., "Influence of amylose-flavor complexation on build-up and breakdown of starch structures in aqueous food model systems", LWT-Food Science and Technology, Academic Press, United Kingdom, vol. 38, No. 8, ISSN: 0023-6438, XP004951630, Dec. 1, 2005, pp. 885-894.

\* cited by examiner

*Primary Examiner* — Frederick F Krass
*Assistant Examiner* — Ashlee E Wertz
(74) *Attorney, Agent, or Firm* — NIXON & VANDERHYE

(57) ABSTRACT

Disclosed is method for the preparation of an amylose/carotenoid complex including the steps of a) heating a first composition in powder form including amylose or one of its derivatives, so that this amylose changes to amorphous form; and b) mixing the first composition obtained at the end of step a) with a second composition in powder form including at least one carotenoid-type pigment so as to enable the heating of the mixture between 30 and 70° C. to allow the passage to the V conformation of the amylose or one of its derivatives during the complexation of the latter with the carotenoid type pigment, until a homogeneous powders mixture is obtained; compositions which can be obtained by such a method as well as the use of such compositions in the fields of printing, writing, tattooing or make-up.

13 Claims, 2 Drawing Sheets

AMYLOSE/CAROTENOIDS COMPLEXATION PROCESS

CROSS-REFERENCE TO PRIORITY APPLICATIONS

The present patent application claims the U.S. national phase of International Application No. PCT/EP2021/058592 filed Apr. 1, 2021 which designated the U.S. and claims the priority of French FR patent application FR 2003267 filed on Apr. 1, 2020, the entire contents of each of which are hereby incorporated by reference.

BACKGROUND OF THE INVENTION

Field of the Invention

The invention falls within the cosmetics general domain and more specifically in the makeup and tattoo domains

DESCRIPTION OF THE RELATED ART

The tattoo is an ancestral art whose roots have been lost over the centuries. The oldest tattoos observed come from the OTZI mummy dating from 5,300 years ago.

Tattoos have various origins from different cultures, the most characterized movements, among them include Polynesian tattooing, Chinese tattooing, Japanese tattooing and Arabic tattooing.

The most used color in tattooing is the black. If the black inks compositions have evolved over time, the pigments traditionally used are black charcoal, animal charcoal, soot and spindle. Classical black inks still mainly use carbon to obtain black pigments.

Among the color pigments currently used, organic molecules having azo groups (—N═N—), aromatic rings and long aromatic chains are used. Mention may be made of the family of diarylides, disazopyrazolones, benzimidazolones, naphthols, phtalocyanines and quinacridones. Metal oxides are also used for certain colors (ferrocyanides and ferricyanides in particular).

The pigments are in the form of particles around 100 nm. Their large size prevents them from being assimilated and broken down by macrophages in the dermis, which allows them to remain fixed in the skin indefinitely.

These pigments are very often associated with titanium and aluminum oxide with the aim of improving the color rendering of the tattoo. These have opacifying properties. One can also find traces of heavy metals in these pigments, such as Mercury, Lead, Cadmium, Nickel, Zinc, Chromium, Cobalt, Titanium, Aluminum, Iron, Copper, Barium and Antimony. The presence of these metals in these inks, sometimes in quantities exceeding the thresholds allowed by cosmetics legislation, raises questions about the harmlessness of these products once injected into the dermis, even if no toxicity has been however observed on these inks present in the body.

Tattoos are used for various reasons, mainly for ornamentation of the skin. While tattoos have traditionally been applied as models for the skin, they are also used for permanent cosmetics, such as eyeliner and lip color, often by people who cannot wear makeup, such as those suffering from arthritis or Parkinson's disease. Tattoos are also used for the identification and marking of pets but also in the food industry for the traceability of meat and animal products such as eggs. The tattoo even sees its use extended to modern medicine, in particular in radiotherapy for the marking of the regions to be treated on the body.

It would therefore be advantageous to develop an ink which is not harmful to the human body for which it is intended and which allows good, stable rendering over time of the color of the pigment or pigments which it comprises.

SUMMARY OF THE INVENTION

The complexation of starch amylose with carotenoids, as with many other molecules, has been described in the prior art. Such a complexation then makes it possible to improve the stability of these carotenoids. Now, the complexation reaction of these carotenoids with the starch molecules takes place in solution and at a high temperature (90° C.). Such a reaction not only leads to the degradation of a large part of the carotenoids, due to their fragility, but it also results in a heterogeneous solution in terms of its structure, but also in its appearance, wherein a large part of the carotenoids is not in a complexed form. Finally, such a solution, in addition to its mediocre yield, is so imperfect that it is of no industrial use.

The inventor has been able to demonstrate that a complexation reaction between amylose in V conformation, obtained by heating a solid composition in powder form comprising amylose, makes it possible to obtain completely both a very good complexation of the carotenoids without degrading them by being mixed with a composition containing them and also being in powder form.

Consequently, a first object of the invention relates to a method for the preparation of an amylose/carotenoid complex comprising the steps of:

A) heating a first composition in powder form comprising amylose or one of its derivatives, so that this amylose changes to amorphous form; and B) mixing the first composition obtained at the end of step A) with a second composition in powder form comprising at least one carotenoid-type pigment so as to enable the heating of the mixture between 30 and 70° C. to allow the passage to the V conformation of the amylose or one of its derivatives during the complexation of the latter with the carotenoid type pigment, until a homogeneous powders mixture is obtained.

Optionally, the method according to the invention further comprises a step C) consecutive or concomitant with step B) of adding at least one solvent to obtain a composition in liquid form comprising at least one complex amylose/carotenoid.

A second object of the invention relates to a composition, which can be obtained by the method according to the invention, which composition comprises at least one amylose/carotenoid complex.

Preferably, this solid composition comprises less than 40% carotenoid in non-complexed form, preferably less than 20% and, in a particularly preferred manner, less than 10% carotenoid is in a non-complexed form.

A third object of the invention relates to a composition in liquid form, which can be obtained by the method of to the invention, which composition comprises at least one amylose/carotenoid complex.

Preferably, this composition in liquid form comprises less than 40% carotenoid in a non-complexed form, preferably less than 20% and, in a particularly preferred manner, less than 10% carotenoid in a non-complexed form.

Such compositions can be used in the cosmetic field, in particular tattooing or make-up, or even in the field of printing.

According to a fourth aspect, the present invention therefore relates to the use of a composition as described above in a printing or writing ink.

According to a fifth aspect, the present invention is finally aimed at the use of a composition as described above for tattooing and/or makeup.

BRIEF DESCRIPTION OF THE DRAWINGS

The invention will be better understood on reading the following description, given by way of non-limiting example, and made with reference to the figures representing.

In these figures, identical reference numerals from one figure to another designate identical or similar elements. Also, for reasons of clarity, the drawings are not to scale, unless otherwise stated.

DESCRIPTION OF THE PREFERRED EMBODIMENTS

As mentioned above, a first object of the invention relates to a method for the preparation of an amylose/carotenoid complex comprising the steps of:

A) heating a first composition in powder form comprising amylose or one of its derivatives, so that this amylose changes to amorphous form; and B) mixing the first composition obtained at the end of step A) with a second composition in powder form comprising at least one carotenoid-type pigment so as to enable the heating of the mixture between 30 and 70° C. to allow the passage to the V conformation of the amylose or one of its derivatives during the complexation of the latter with the carotenoid type pigment, until a homogeneous powders mixture is obtained.

By composition in powder form is meant a solid composition whose particle size is comprised between 10 μm and 100 μm, preferably between 15 μm and 50 μm.

Amylose (branched polymer of α-D-glucopyranose) is one of the main components of starch with amylopectin (linear polymer of α-D-glucopyranose).

Figure 1:
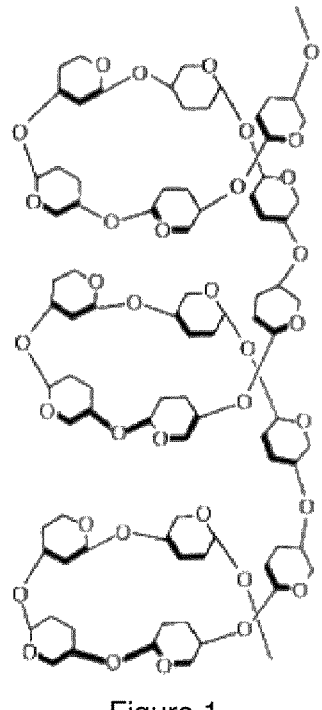
FIG. 1 is a representation illustrating an amylose molecule in V conformation (V-amylose).

In detail, amylose is an essentially linear molecule composed of 500 to 600 units of α-D-glucopyranose, distributed over 1 to 20 different chains with an average degree of polymerization of 500. The molar mass amylose is usually $2 \times 10^5$ to $2 \times 10^6$ g/mol and depends on the botanical origin and also on the used fractionation method. Now, an amylose population is heterogeneous, with a polydispersity usually between 1.3 and 2.1, but sometimes reaching higher values (5-10). In terms of molecular structure, amylose has a helical shape, as shown in FIG. 1. In aqueous medium, it associates with another amylose molecule to form a double helix, the helices organizing themselves according to different conformations (we speak of A or B type conformations).

Now, there are single amylose molecules (i.e. not dimerized). Then, we speak of V conformation (or V-amylose), which is also in helical form.

This conformation is also important since it allows to structure the starch via the association of this V-amylose with amylopectin. Amylose, and more specifically V-amylose, is known for its ability to form stable complexes with other molecules.

Finally, amylose also includes an amorphous form, which is an unstructured form, and which is therefore not in a helical form.

The transition from the A or B type amylose conformation to a V type conformation requires the passage through the amorphous conformation.

Step B) of mixing amylose or one of its derivatives in amorphous form, at the end of step A, with at least one carotenoid-type pigment allows the change to V-amylose conformation during the complexation of the latter with the pigment of the carotenoid type.

The starch comprising this amylose is present in many cereals and plants and corresponds to the association of two homopolymers in variable proportions Depending on the starch origin, the amylose and amylopectin proportion varies. There is thus 72 to 80% amylopectin and 20 to 28% amylose in wheat and potatoes. For rice, sorghum or rye, there is 94% amylopectin for 6% amylose.

Also, mention may be made for a composition comprising amylose of both pure amylose and of modified or unmodified rice, wheat or even sorghum starch.

By amylose derivative is meant an amylose polymer whose hydroxyl groups at the end of the chain have been replaced by a group chosen from the group comprising terti-butoxide, iso-propanolate, 3-ethylpentan-3-olate, 4-propylheptan-4-olate, and 5-butylundecan-5-olate. Such groups are bulky and thus make it possible to avoid natural degradation of the amylose derivative by α-amylase or β-amylase, which enzymes are naturally present in the human body.

By amylose derivative is also meant an amylose polymer whose at least one of the internal hydroxyl groups, as opposed to the hydroxyl groups at the end of the chain, has been replaced by a group chosen from the group comprising acetate, ethanolate, 2-hydroxyethoxide, methacrylate, methyl methacrylate, tartrate, cysteine ester, and (2-Dodecen-1-yl) succinic anhydride ester. Such groups make it possible to improve the stability and the hold of the amylose derivative, whether in the dermis for a tattoo application or for another cosmetic application.

By amylose derivative is further meant an amylose polymer whose at least one of the hydroxyl groups has undergone an esterification reaction with a compound chosen from the group comprising citric acid, malic acid, lactic acid, glycolic acid, arginine, histidine, lysine, aspartic acid, glutamic acid, serine, threonine, asparagine, glutamine, cysteine, glycine, proline, alanine, valine, isoleucine, methionine, tyrosine, tryptophan, (9Z,12Z)-octadeca-9,12-dienoic acid, (9Z,12Z, 15Z) acid-octadeca-9,12,15-trienoic acid, (5Z,8Z,11Z, 14Z,17Z)-icosa-5,8,11,14,17-pentaenoic acid, cis-9-octadecamonoenoic acid, icos-11-enoic acid, 13-docosenoic acid, hexanoic acid, octanoic acid, linoleic acid, O-phosphoserine and any molecule belonging to the phosphatidylserine group.

The first composition comprises an amylose content comprised between 5% and 100%, preferably between 20% and 90% and, particularly preferably between 50 and 70% (by weight relative to the total weight of the first composition).

Ideally, this first composition also comprises amylopectin which, is naturally present in starch, and plays a stabilizing and texturizing role with the composition obtained by the method of the invention.

When the first composition comprises amylopectin, the first composition will advantageously comprise an amylopectin content comprised between 20% and 70% with an amylose content comprised between 30 and 80%, preferably an amylopectin content comprised between 30% and 50% with an amylose content comprised between 50 and 70% (by weight relative to the total weight of the first composition).

The heating step allowing the passage of the amylose into an amorphous conformation can be carried out by techniques well known to those skilled in the art.

This heating step is advantageously carried out so as to administer to the first composition an energy of between $5 \times 10^2$ J/gram of amylose and $5 \times 10^6$ J/gram of amylose, preferably between $1 \times 10^5$ J/gram of amylose and $1 \times 10^6$ J/gram of amylose, and particularly preferably between $5 \times 10^5$ J/gram of amylose and $1 \times 10^6$ J/gram of amylose.

This heating step is advantageously carried out by exposing the first composition to microwave radiation.

Preferably, a microwave frequency corresponding to the best reactivity of the amylose will be used. Typically, the microwave frequency used is comprised between 2.4 and 2.5 GHz, the optimum frequency range is comprised between 2.44 and 2.46 GHz.

By way of example, such a heating step could be carried out by a microwave at a power of 750 W for ten minutes for a composition comprising 500 mg of amylose.

In the present application, the term "carotenoid-type" pigment means a pigment belonging to the family of carotenoids.

Carotenoids are a family of molecules present in many plants and animals.

Carotenoids also have the particularity of existing in several different colors. This makes it possible to envisage an infinite palette of colors by combining these pigments.

Carotenoids include the family of carotenes (without an oxygen atom in its structure) and the xanthophylls (having at least one oxygen atom in its structure).

The at least one carotenoid-type pigment for the second composition is preferably chosen from β-carotene, lutein, lycopene, astaxanthin, astacene, neoxanthin, canthaxanthin, fucoxanthin, violerythrin, α-carotene, zeaxanthin, rhodoxanthin, β-Cryptoxanthin, and mixtures thereof.

Depending on the concentrations of these pigments as well as by making mixtures of these different pigments, it is possible to simply obtain an infinity of colors, including black which is the color most used in tattooing.

The mixing step can be carried out by techniques well known to those skilled in the art.

Typically, this mixture can be made by means of a ball or pestle mill, a mixer with horizontal or vertical axes, or even an endless screw.

The mixture heating in step B) makes it possible to potentiate the complexation of the amylose and of the carotenoid.

Typically, this mixture heating is comprised between 30 and 60° C., preferably between 40 and 60° C. and, in a particularly preferred manner, between 40 and 50° C.

Such a temperature interval has the advantage of improving the complexation yield, while limiting the carotenoid destabilization.

Figure 2:
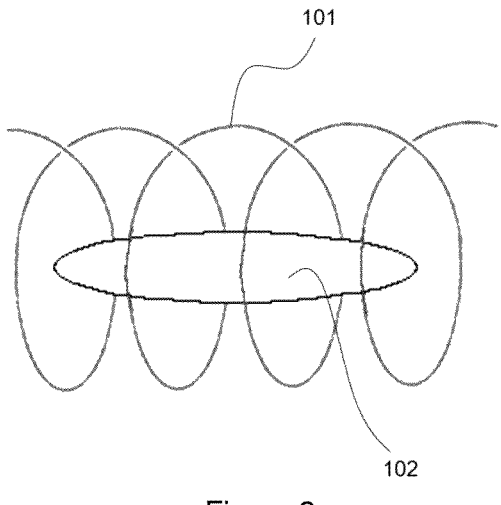
FIG. 2 is a diagram illustrating a starchy biopolymer in which amylose is complexed with a carotenoid pigment.

Advantageously, the step B) of mixing is carried out to obtain an amylose/carotenoid mass ratio equal to the following formula:

$$15.9 \times \frac{M\beta - \text{carotene}}{M\text{carotenoid}} \qquad \text{[Math. 1]}$$

wherein "Mcarotenoid" represents the molar mass of carotenoid in g/mol, and "Mβ-carotene" is the molar mass of β-carotene and is equal to 536.9 g/mol. This mass ratio makes it possible to best saturate the amylose cavity with the carotenoid-type pigment and therefore to obtain a good coloration while avoiding loss of carotenoid-type pigment (excess pigment not complexed with amylose). The FIG. 2 schematically illustrates a starch polymer in which amylose 101 is complexed with a carotenoid pigment 102. In fact, V-amylose is amphiphilic in nature. Thus, it has a hydrophilic surface, allowing its solubility in water, as well as a hydrophobic cavity inside its helix. It appears that the carotenoids, which are highly lipophilic molecules with an elongated and rectilinear structure, come to lodge in a very stable manner within this cavity.

This complexation can be deduced using a device analyzing the circular dichroism of amylose. The amylose helix is a left-handed helix exhibiting an observable chirality through circular dichroism. In addition, the presence of a complexed carotenoid type pigment inside this helix will change the amylose dichroism to show a particular dichroism. This allows to identify quickly and precisely the presence of this complex.

Figure 3:
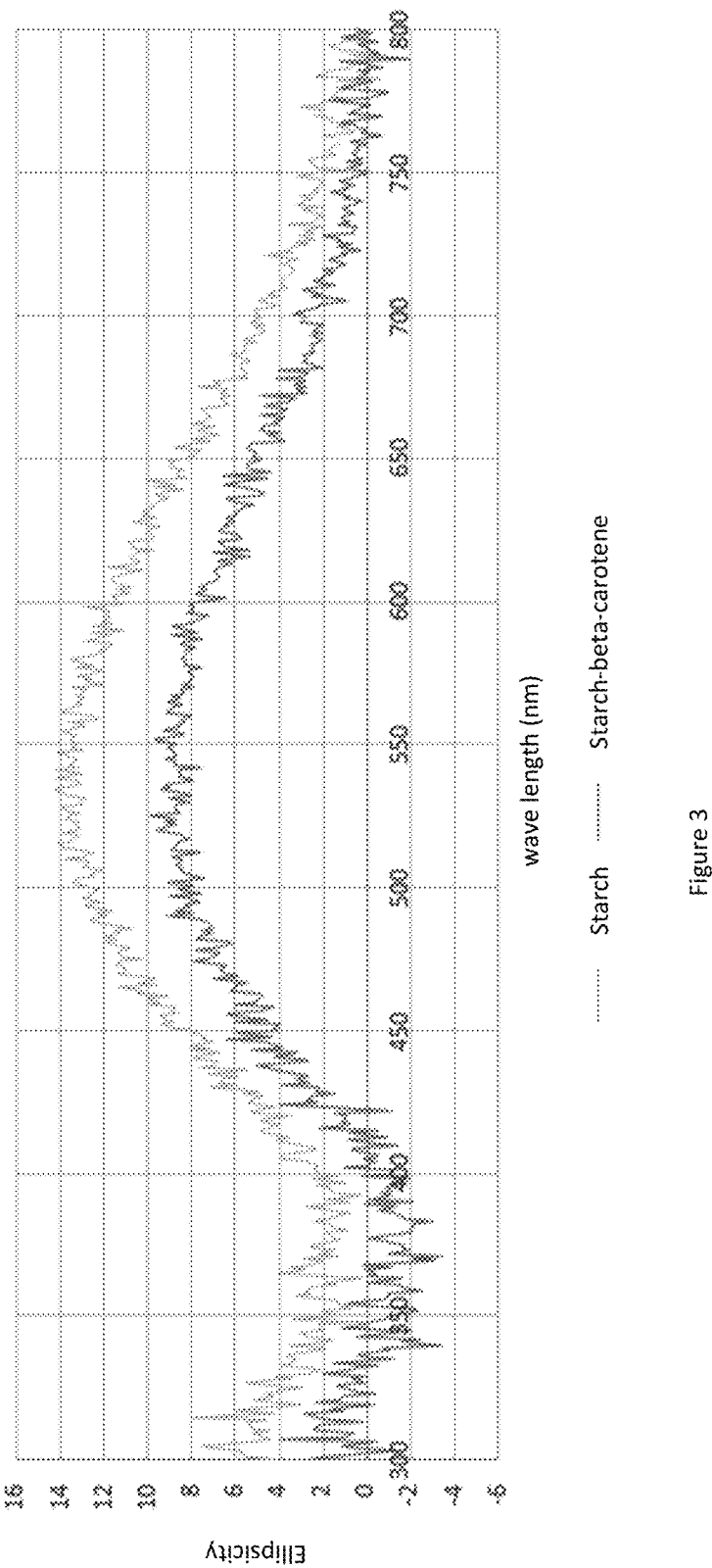
FIG. 3 is a graph illustrating the ellipticity of the starch biopolymer (light gray curve) and of the starch biopolymer in which amylose is complexed with one of β-carotene (dark gray curve), as a function of the wavelength. This graph makes it possible to observe the changes in circular dichroism of amylose depending on whether or not it is complexed with β-carotene.

In order to verify this complexation, the following experiment is carried out:

A 10% mass aqueous solution of starch and an aqueous solution of 10% mass starch and a β-carotene concentration equal to $1.4 \times 10^{-4}$ mol/L are prepared. These solutions are then deposited in circular dichroism analysis cells, at a temperature of 20° C. The results are illustrated in FIG. 3 representing a graph illustrating the ellipticity of the starch polymer (light gray curve) and of the starch polymer in which the amylose is complexed with a β-carotene (dark gray curve), in function of the wavelength. It can be seen that the 2 curves are quite different, thus showing a difference in circular dichroism between the starch polymer alone and the starch polymer whose amylose is complexed with the β-carotene pigment. β-carotene does not exhibit circular dichroism alone, in aqueous solution or in a less polar solvent.

According to a particular embodiment, the method of the invention further comprises a step C) consecutive to or concomitant with step B) of adding at least one solvent to obtain a composition in liquid form comprising at least one amylose/carotenoid complex.

In one embodiment, step C) of adding at least one solvent will follow step B) of mixing, for example by dry grinding.

In another embodiment, the step C) of adding at least one solvent will be simultaneous with step B) of mixing, preferably this step C) of addition will also be progressive.

The gradual addition of solvent makes it possible to solubilize the amylose and fix its conformation while avoiding losses of pigment of the carotenoid type not complexed in the solvent.

Typically, the used solvent is a polar solvent.

"Polar solvent" means a solvent consisting of molecules having a dipole moment. This polar solvent can be protic or aprotic depending on whether or not it is able to release acidic H+ ions.

By way of example of aprotic polar solvent, mention may be made of ketones (e.g. acetone or butanone), sulfoxides (e.g. DMSO), N, N disubstituted amides (N,N dimethyl formamide), nitriles (e.g. acetonitrile), esters (e.g. ethyl acetate), tertiary amines (e.g. triethylamine), nitrogen heterocycles (e.g. pyridine).

By way of example of a polar protic solvent, mention may be made of water, alcohols, carboxylic acids (e.g. formic acid and acetic acid) or primary and secondary amines.

Preferably, the polar solvent used will be a protic polar solvent and, among them, it will be preferred to use an alcohol.

Among the alcohols that can be used, mention may be made of methanol, ethanol, glycol, propylene glycol, glycerol, or else isopropanol.

A solvent that is particularly acceptable for cosmetic use, even if in the form of traces, can be chosen from ethanol, glycol, glycerol, propylene glycol and isopropanol.

Preferably, the solvent comprises between 90% and 100% of water, between 0% and 10% of ethanol, between 0% and 10% of glycerol and between 0% and 10% of isopropanol.

Preferably, the solvent represents from 50% to 90% by weight of the liquid composition comprising an amylose/carotenoid complex, preferably from 60% to 85% by weight, more preferably from 70% to 80% by weight. According to a preferred embodiment, the solvent represents 80% by weight of the liquid composition comprising an amylose/carotenoid complex.

A second object of the invention relates to a solid composition in powder form which can be obtained by the method of the invention, which solid composition comprises at least one amylose/carotenoid complex and less than 20% of the at least one carotenoid-type pigment in its degraded form, preferably less than 10%, and particularly preferably less than 5%.

The very high efficiency of the method of the invention at a low complexation temperature makes it possible to considerably limit the degradation of the carotenoids. As a result, the obtained composition comprises a very small proportion of degraded carotenoids.

By pigment of the carotenoid type in degraded form is meant a pigment whose initial structure has been modified, typically by the destruction of at least one bond, preferably of at least one double bond. The destruction of this bond generally leads to the loss of one or more groups.

By carotenoid-type pigment in degraded form, is meant a molecule which has lost all or part of its initial absorbance capacities.

The obtained solid composition is homogeneous. It indeed has a homogeneous color due to the very good complexation of the carotenoid with amylose and thus, its good dispersion in the compositions.

Preferably, this solid composition comprises less than 50% carotenoid in non-complexed form (by weight relative to the total weight of the composition), preferably less than 25% and, particularly preferably, less than 10% carotenoid in non-complexed form.

The polyisoprenoic structure characteristic of carotenoids gives them numerous properties but is also responsible for their great sensitivity to degradation in the presence of various factors. The unsaturations of the linear chain are as many places of possible degradation. The central cleavage of β-carotene produces, for example, retinal (vitamin A). Depending on the carotenoids, terminal groups can also be degraded under certain conditions, releasing shorter chain compounds with terminal aldehyde or ketone functions. The sources of carotenoid oxidation are diverse and determine the mechanisms involved and the nature of the products formed. However, the degradation agents are often multiple and, once the oxidation has been initiated, the carotenoids can also react with the newly formed products. In natural environments, the products derived from the degradation of carotenoids can then be extremely numerous and varied.

A third subject of the invention relates to a composition in liquid form which can be obtained by the method of the invention, which composition comprises at least one amylose/carotenoid complex and less than 20% of the at least one pigment carotenoid type in degraded form, preferably less than 10%, and particularly preferably less than 5%.

Naturally, this amylose/carotenoid complex is in solution in a solvent as defined above.

Here again, the obtained composition is homogeneous.

Methods in liquid media in the presence of amylose cause the mixture to gel, which complicates its use.

The composition in liquid form of the invention is not, in essence, in the form of a gel.

Advantageously, the viscosity of the composition of the invention is less than 0.1 Pa·s, preferably comprised between 0.01 and 0.001 Pa·s.

Preferably, this composition in liquid form comprises less than 20% of carotenoid in non-complexed form (by weight relative to the total weight of the composition), preferably less than 10% and, particularly preferably, less than 5% carotenoid in non-complexed form.

The amylose concentration complexed with carotenoid-type pigment is preferably between 10 g/L and 500 g/L of composition in liquid form. This concentration range makes it possible to obtain a composition for obtaining a visible tattoo when the composition is injected into the dermis.

Preferably, the composition comprises starch, which starch is present at a mass concentration comprised between 150 g/L and 250 g/L of composition in liquid form. This concentration scale makes it possible to obtain good staying power and good viscosity of the ink composition for its use in a tattoo ink.

More preferably, the carotenoid molar concentration for the composition in liquid form for a tattoo is preferably comprised between $1.17\times10^{-3}$ mol/L and $5.86\times10^{-2}$ mol/L, more preferably still comprised between $1.76\times10^{-2}$ mol/L and $2.93\times10^{-2}$ mol/L. This concentration range makes it possible to have a clearly visible and satisfactory coloring in terms of color rendering while avoiding having a reflux of pigments which agglomerates. A concentration of pigment that is too low leads to poor coloring while a concentration that is too high leads to a deposit of pigment on the surface of the ink composition.

The compositions of the invention may also comprise one or more adjuvants such as a preservative, a plasticizer, a thickener, an emulsifier, or any other adjuvant conventionally used in the field of tattooing, makeup or printing.

A preservative may be chosen from the group comprising polyaminopropyl biguanide and 1-[3,4-bis(hydroxymethyl)-2,5-dioxoimidazolidin-4-yl]-1,3-bis(hydroxymethyl)urea.

A thickener may be chosen from the group comprising dextrin, amylopectin and xanthan gum.

An emulsifier may be chosen from the group comprising soy lecithin, polysorbate 20, polysorbate 60 and polysorbate 80.

Such compositions can be used in the cosmetics field, in particular tattooing or make-up, or even in the field of printing.

According to a fourth aspect, the present invention therefore relates to the use of a composition as described above in a printing or writing ink.

According to a fifth aspect, the present invention finally relates to the use of a composition as described above for tattooing and/or for makeup.

The invention will be better understood in the light of the following examples, which are given for purely illustrative purposes only and are not intended to limit the scope of the invention, defined by the annexed claims.

Examples of Tattoo Ink Composition Synthesis

Synthesis of Orange Ink with β-Carotene

In a container provided for this purpose, grind 250 mg of corn starch to obtain a homogeneous powder.

Treat the starch in microwave at 750 W for 10 minutes. This treatment makes it possible to change the amylose conformation, passing from a double helix conformation (A or B amylose) to a single helix conformation (V amylose) without changing its chemical structure.

Place the treated starch while still hot in a mortar and deposit 15.7 mg of β-carotene.

Grind vigorously using a pestle until a homogeneous powder is obtained. Solid phase complexation improves the complexation yield.

Add 1.25 mL of distilled water to the mortar and grind vigorously until a homogeneous viscous fluid is obtained. The gradual addition of water makes it possible to solubilize the amylose and fix its conformation by avoiding losses of carotenoid in the aqueous medium.

Add 1.25 mL of water, mix with the pestle until a homogeneous solution is obtained and the complex is completely dissolved.

Take the tattoo ink composition thus obtained and store it in an opaque bottle.

Synthesis of Yellow Ink

In a container provided for this purpose, grind 250 mg of corn starch to obtain a homogeneous powder.

Treat the starch in microwave at 750 W for 10 minutes.

Place the treated starch while still hot in a mortar and place 16.6 mg of Lutein.

Grind vigorously using a pestle until a homogeneous powder is obtained.

Add 1.25 mL of distilled water to the mortar and grind vigorously until a homogeneous viscous fluid is obtained.

Add 1.25 mL of water, mix with the pestle until a homogeneous solution is obtained and the complex is completely dissolved.

Take the tattoo ink composition thus obtained and store it in an opaque bottle.

Synthesis of Red Ink

In a container provided for this purpose, grind 250 mg of corn starch to obtain a homogeneous powder.

Treat the starch in microwave at 750 W for 10 minutes.

Place the still hot treated starch in a mortar and place 15.7 mg of Lycopene.

Grind vigorously using a pestle until a homogeneous powder is obtained.

Add 1.25 mL of distilled water to the mortar and grind vigorously until a homogeneous viscous fluid is obtained.

Take the tattoo ink composition thus obtained and store it in an opaque bottle.

Blue Ink Synthesis

In a container provided for this purpose, grind 250 mg of corn starch to obtain a homogeneous powder.

Treat the starch in microwave at 750 W for 10 minutes.

Place the treated starch while still hot in a mortar and place 17.4 mg of Violerythrine.

Grind vigorously using a pestle until a homogeneous powder is obtained.

Add 1.25 mL of distilled water to the mortar and grind vigorously until a homogeneous viscous fluid is obtained.

Add 1.25 mL of water, mix with the pestle until a homogeneous solution is obtained and the complex is completely dissolved.

Take the tattoo ink composition thus obtained and store it in an opaque bottle.

Synthesis of Black Ink

In a container provided for this purpose, grind 250 mg of corn starch to obtain a homogeneous powder.

Treat the starch in microwave at 750 W for 10 minutes.

Place the treated starch while still hot in a mortar and place 5.54 mg of Lutein, 5.23 mg of Lycopene and 5.50 mg of Violerythrine.

Grind vigorously using a pestle until a homogeneous powder is obtained.

Add 1.25 mL of distilled water to the mortar and grind vigorously until a homogeneous viscous fluid is obtained.

Add 1.25 mL of water, mix with the pestle until a homogeneous solution is obtained and the complex is completely dissolved.

Add 1.25 mL of water, mix with the pestle until a homogeneous solution is obtained and the complex is completely dissolved.

Take the tattoo ink composition thus obtained and store it in an opaque bottle.

Complexation in Liquid Medium (Protocol 1)

In a 100 mL flask, place 2.00 g of corn starch (30% amylose and 70% amylopectin) with 18.0 mL of distilled water. Shake continuously.

Bring the solution to 60° C., then add 126 mg of powdered β-carotene. Leave to stir for one hour.

Observations: The solution is inhomogeneous and a large quantity of β-carotene particles in suspension or stuck to the wall of the flask is observed. There is no orange color that would indicate the presence of a stable starch/β-carotene complex or formulation.

Once cooled, circular dichroism analyzes of the solution show a behavior of the starch similar to that of an aqueous solution of corn starch alone.

Complexation in Liquid Medium (Protocol 2)

In a 100 mL flask, place 2.00 g of corn starch (30% amylose and 70% amylopectin) with 18.0 mL of distilled water. Shake continuously.

Bring the solution to 70° C., then add 126 mg of powdered β-carotene. Leave to stir for one hour.

Observations: the solution becomes slightly orange. A part must have complexed but there remain red particles on the surface and in solution, proof of the non-complexation of a large part of the carotenoid. It is impossible to quantitatively and qualitatively observe the complexation via analysis because once cooled, the starch forms a thick hydrogel. The β-carotene particles are trapped inside and form an inhomogeneous and unusable result. It could be envisaged to dilute this gel in water to evacuate the non-complexed β-carotene and then carry out vacuum evaporation of the remaining starch/β-carotene mixture until a satisfactory concentration is obtained, or even a solid product is obtained, but these steps are too tedious to carry out at an industrial level, and the quantity of carotenoid is insufficient to obtain satisfactory color rendering.

Measurement of the Non-Complexed β-Carotenoid Amount

In a flask at ambient temperature and under a nitrogenous atmosphere, 1 mL of hexane and 1 mL of aqueous solution at 10% by mass of starch/β-carotene complex prepared according to method of the invention or according to the liquid medium complexation protocols.

The mixture is then left to stir for 24 hours away from light.

The mixture is then decanted and the colored organic phase loaded with β-carotene is recovered, which β-carotene corresponds to free β-carotene not complexed with amylose.

A colorimetric titration of the β-carotene recovered from measured solutions of β-carotene in hexane is then carried out.

The results show that the method of the invention allows the complexation of almost all of the β-carotene with amylose, whereas well over 20% of the β-carotene is in the non-complexed form with the liquid medium complexation protocols.

Characterization and Measurement of the β-Carotene Degradation Residues Quantity From the mixtures made previously, the rotary evaporation of the aqueous and organic phases is carried out.

$^1$H NMR spectrometry is then carried out on the powders obtained from the aqueous phase, with deuterated water ($D_2O$) and from the organic phase with deuterated trichloromethane ($CDCl_3$).

The results show that less than 5% of at least one carotenoid-type pigment is in degraded form.

Unsuitable Solvents

The use of solvents in which the carotenoids are soluble to allow the meeting of a carotenoid (most often β-carotene) and amylose in an aqueous medium are unsuitable for the production of cosmetic products on an industrial basis.

Organic solvents such as methanol, or dichloromethane used for the production of formulations between β-carotene and polysaccharides already existing in the literature require costly and tedious purification steps to get rid of them once the formulation has been made. Moreover, since these solvents are harmful to health, it is unthinkable to produce complexes containing traces of these solvents for cosmetic use.

Non-harmful organic solvents have been tested for the production of complexes between carotenoids and amylose. Ethanol and acetone have been tested for this purpose. But amylose is not soluble in these solvents, it is then impossible to obtain a complexation with a satisfactory yield. Indeed, the observable complexation yield is less than 50%. The non-complexed carotene is then quickly found in the form of degradation products.

Administration of the Composition of the Invention in a Skin Model

Injection Protocol on Human Skin

Made from the orange ink shown in the examples of tattoo ink composition synthesis above.

Protocol carried out on samples of human skin in a survival medium known as NATIVESKIN®.

Injection Via Dermograph:

10 μL of ink is injected into a skin sample with a dermograph comprising a "liner" type needle with 6 points. The injection must perforate the epidermis so that the solution lodges in the dermis.

Clean the excess ink by passing a dry absorbent paper over the skin.

Injection Via Transdermal Syringe:

10 μL of ink is injected into the skin sample with a micro-syringe on the side of a biopsy to inject the solution directly into the dermis, without perforating the epidermis.

The skin models are left in 1 mL of NATIVESKIN® medium in cell culture conditions (37° C., 5% CO2, maximum humidity) with renewal of the medium every day.

Biopsies are carried out every day to observe the ink evolution in the skin, as well as the good healing of the skin for the protocol carried out with a dermograph.

More generally, it should be noted that the embodiments and embodiments of the invention considered above have been described by way of non-limiting examples and that other variants are therefore possible. The ink composition can for example be used for a make-up composition (lipsticks, face powders, eye pencils, etc.), for a cosmetic composition (hygiene products, skin care products, face or body, hair products, perfumes, sunscreen products, shaving products, etc.) or even for printing or writing ink.

The invention claimed is:

1. A method for the preparation of an amylose/carotenoid complex, said amylose/carotenoid complex consisting of 1) one carotenoid-pigment and of 2) amylose or a derivative of amylose, said method comprising:

a) heating a first composition in powder form comprising amylose or a derivative of amylose, so that this amylose changes to amorphous form; and b) mixing the first composition obtained at the end of step a) with a second composition in powder form comprising at least one carotenoid pigment, where the mixture is heated between 30° and 70° C. to allow the passage to the V conformation of the amylose or a derivative of amylose during complexation of the amylose or a derivative of amylose with the carotenoid pigment, until a homogeneous powders mixture is obtained, whose mixture is a solid composition having a homogenous color said homogeneous color being due to complexation of the carotenoid pigment with amylose with less than 10% carotenoid pigment in non-complexed form together with less than 10% of said at least one carotenoid pigment in degraded form.

2. The method of claim 1, wherein the first composition further comprises amylopectin.

3. The method of claim 1, wherein step a) of heating corresponds to the administration to the first composition of an energy comprised between $10^3$ and $5\times10^6$ J/gram of amylose or of the derivative of amylose.

4. The method according to claim 1, wherein the mixture is heated between 3° and 60° C. in step b).

5. The method according to claim 1, further comprising a step c) consecutive or concomitant to step b) of adding at least one solvent for obtaining a composition in liquid form comprising at least one amylose/carotenoid complex.

6. The method of claim 1, wherein step a) of heating corresponds to the administration to the first composition of an energy comprised between $2\times10^5$ and $2\times10^6$ J/gram of amylose or of the derivative of amylose.

7. The method according to claim 1, wherein the mixture is heated between 4° and 60° C. in step b).

8. The method of claim 3, wherein step a) of heating is carried out by exposing the first composition to microwave radiation.

9. The method of claim 8, wherein the microwave frequency used is comprised between 2.4 and 2.5 GHz.

10. The method of claim 1, wherein the first composition comprises an amylose content comprised between 20% and 90% by weight relative to the total weight of the first composition.

11. The method of claim 2, wherein the first composition comprises:

an amylopectin content comprised between 20% and 70% by weight relative to the total weight of the first composition, with an amylose content comprised between 80 and 30% by weight relative to the total weight of the first composition.

12. The method of claim 3, wherein the first composition comprises:

an amylopectin content comprised between 30% and 50% by weight relative to the total weight of the first composition, with an amylose content comprised between 70 and 50% by weight relative to the total weight of the first composition.

13. The method of claim 1, wherein the step b) of mixing is carried out to obtain an amylose/carotenoid mass ratio equal to the following formula:

$$\frac{m^{amylose}}{m^{carotenoid}} = 15.9 \times \frac{M\beta-\text{carotene}}{M carotenoid}$$

wherein "Mcarotenoid" represents the molar mass of the carotenoid pigment in g/mol, and "Mβ-carotene" is the molar mass of β-carotene and is equal to 536.9 g/mol.

\* \* \* \* \*